United States Patent [19]
Nguyen et al.

[11] Patent Number: 5,656,145
[45] Date of Patent: Aug. 12, 1997

[54] NEEDLE GUIDE FOR LOADING SAMPLES INTO A VERTICAL SLAB GEL

[75] Inventors: Hoa Nguyen, Pinole; Daniel L. Van Atta, Clayton, both of Calif.

[73] Assignee: Bio-Rad Laboratories, Inc., Hercules, Calif.

[21] Appl. No.: 650,678

[22] Filed: May 20, 1996

[51] Int. Cl.$^6$ .................. G01N 27/26; G01N 27/447
[52] U.S. Cl. .................. 204/618; 204/466; 204/467; 204/616; 204/619; 204/620
[58] Field of Search .................. 204/618, 619, 204/620, 616, 466, 467

[56] References Cited

U.S. PATENT DOCUMENTS

| | | | |
|---|---|---|---|
| 4,574,040 | 3/1986 | Delony et al. | 204/618 X |
| 4,663,015 | 5/1987 | Sleeter et al. | 204/618 |
| 4,975,174 | 12/1990 | Bambeck et al. | 204/618 |
| 5,073,246 | 12/1991 | Chu et al. | 204/619 |
| 5,164,065 | 11/1992 | Bettencourt et al. | 204/619 |
| 5,217,591 | 6/1993 | Gombocz et al. | 204/466 |
| 5,284,565 | 2/1994 | Chu et al. | 204/619 |
| 5,324,412 | 6/1994 | Kolner | 204/619 |
| 5,344,534 | 9/1994 | Danziger | 204/467 |

*Primary Examiner*—Kathryn L. Gorgos
*Assistant Examiner*—John S. Starsiak, Jr.
*Attorney, Agent, or Firm*—Townsend and Townsend and Crew LLP

[57] ABSTRACT

The loading of samples into wells that are formed in a vertical slab gel is facilitated by a needle guide that provides expanded openings that taper toward the wells, the openings being separated by partitions that help the user distinguish between the wells and the barriers of transparent gel material between the wells.

6 Claims, 2 Drawing Sheets

NEEDLE GUIDE FOR LOADING SAMPLES INTO A VERTICAL SLAB GEL

This invention lies in the field of vertical slab gel electrophoresis. In particular, this invention addresses problems associated with the use of wells along the upper edge of the slab gel and the loading of samples into the wells.

BACKGROUND OF THE INVENTION

Vertical slab gel electrophoresis is widely used and of much value in nucleic acid sequencing and in the identification of proteins and other species in biological samples. A problem often encountered in these procedures is the difficulty of loading samples into the sample wells formed along the upper edge of the gel. The wells are small in both length and width and it is difficult to visually distinguish the wells from the clear gel material separating the wells. A syringe is generally used to place the samples in the wells, and the unskilled user with inaccurate placement or a nervous hand may inadvertently place the syringe needle in gel material to one side of a well rather than in the well itself, or break a gel partition. In either case, the differentiation between adjacent sample lanes in the gel will be obscured, and this will impair the user's ability to read the gel accurately at the termination of the experiment.

SUMMARY OF THE INVENTION

These and other difficulties are addressed by the present invention, which resides in a needle guide to help the user direct a syringe needle into a well. The needle guide contains a sloping surface with partitions extending outward from the surface and arranged to conform to the spacing of the wells. The sloping surface forms one wall side of a tapering passage to direct the needle into the wells. Vertical slab gels are frequently held by parallel plates of unequal height with the higher of the two plates serving as a retaining wall for the upper buffer solution chamber. The needle guide in preferred embodiments of this invention utilizes this feature by using the higher plate as one wall of the tapering passage directing the needle into the well. A further feature of the guide is that it is shaped to rest stably along the upper edge of one or both of the parallel plates used to support the gel. In certain embodiments of the invention, the guide is constructed for use with a single gel between two parallel plates, and in other embodiments, the guide is constructed for use with a pair of gels, such as are frequently encountered in electrophoretic cells designed to accommodate two vertical slab gels with a common upper buffer chamber and a common lower buffer chamber.

Details of these and other features and advantages of the invention will become apparent from the description that follows.

DETAILED DESCRIPTION OF THE INVENTION AND PREFERRED EMBODIMENTS

While this invention is susceptible of a variety of embodiments differing in shape, size and other features, the concepts of the invention will be best understood by a detailed examination of specific examples. The drawings depict such examples.

Figure 1:
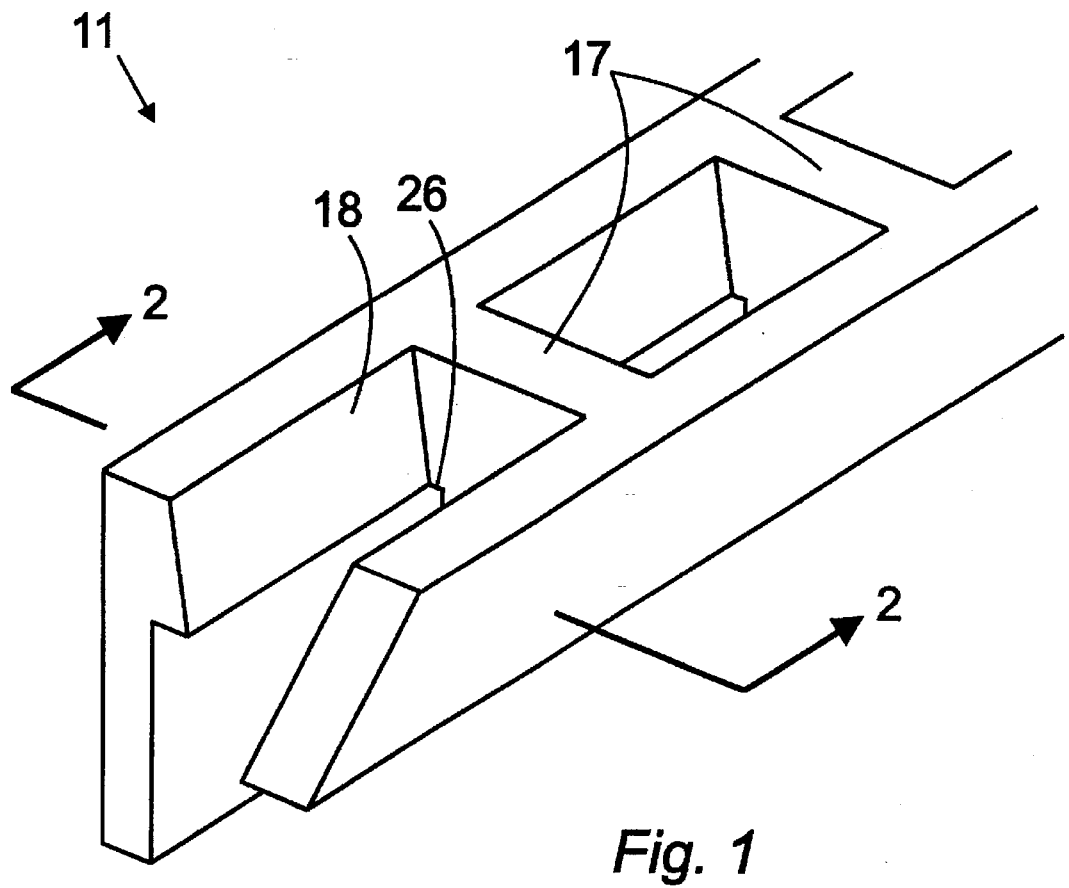
FIG. 1 is a perspective view of a needle guide in accordance with the invention, designed for use with an individual slab gel retained between two plates of unequal height.
Figure 2:
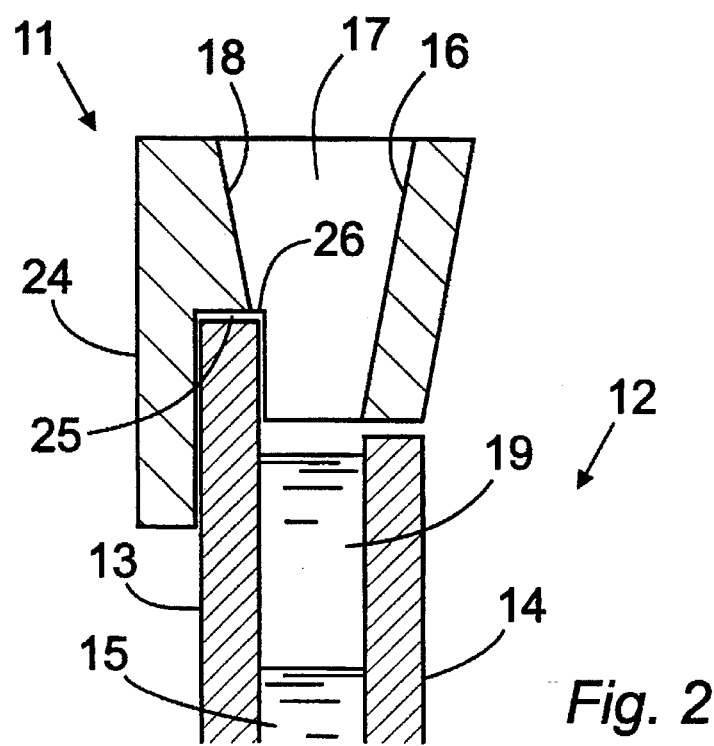
FIG. 2 is a cross section of the needle guide of FIG. 1 taken along the line 2—2 thereof.

FIGS. 1 and 2 depict a needle guide for an individual vertical slab gel held in a gel enclosure that consists primarily of two parallel plates, one of which is taller than the other. The perspective view of FIG. 1 shows the needle guide 11 alone, while the cross section of FIG. 2 shows the needle guide in position over the gel enclosure 12, showing the taller plate 13 and the shorter plate 14 of the enclosure as well as the gel 15. Viewing the two figures together, the needle guide contains a sloping surface 16 and a series of partitions 17 that extend transverse, preferably perpendicular, to the sloping surface. Opposing the sloping surface 16 is a second sloping surface 18. The two sloping surfaces and the partitions thus form a series of tapering passages open at both top and bottom. The spacing of the partitions 17 conforms approximately with the spacing of the gel barriers 19 separating the wells. The spacing between the bottoms of the sloping surfaces, i.e., their smallest horizontal separation, is approximately equal to the spacing between the two gel support plates 13, 14. Thus, the syringe needle containing the sample to be placed in a well is inserted into the wide opening at the top of one of the tapering passages which directs the needle into the well underneath.

The side wall 24 of the needle guide that is placed over the taller plate 13 of the gel enclosure is shaped to form an inverted shoulder 25 which rests upon the top edge of the plate. The partitions likewise have notches 26 to hook over the top edge of the plate. The inverted shoulder and notches together facilitate proper placement of the needle guide over the top of the gel and secure the needle guide into position so that syringes can be inserted without dislocating the guide.

Figure 3:
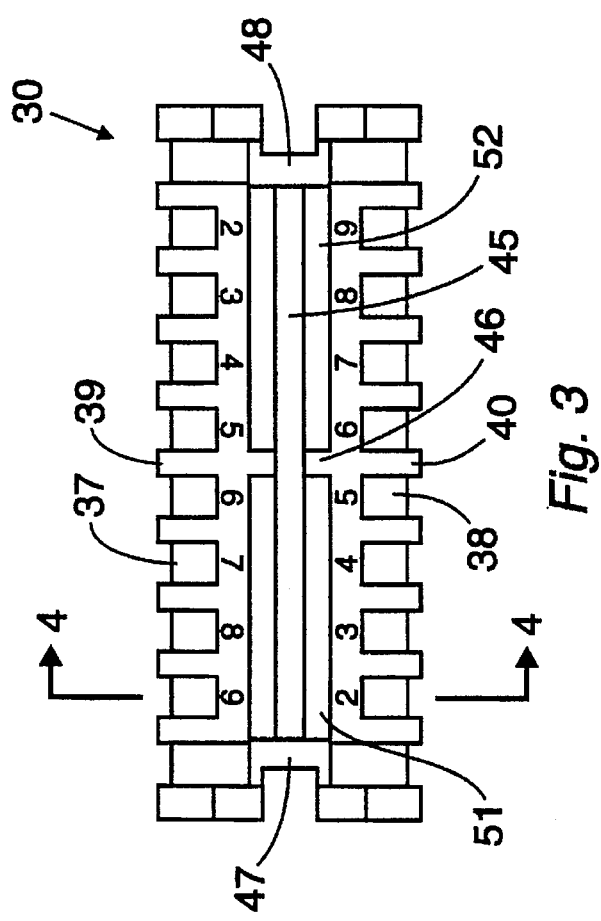
FIG. 3 is a top view of a second needle guide in accordance with the invention, designed for use with a pair of slab gels, both retained between two plates of unequal height.
Figure 5:
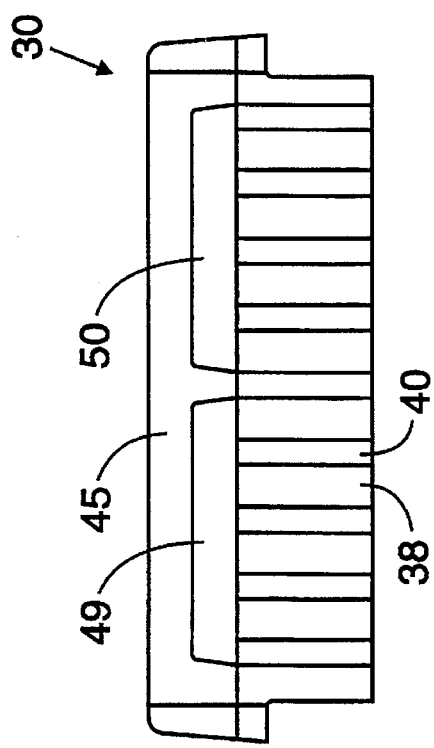
FIG. 5 is a side view of the needle guide of FIGS. 3 and 4.
Figure 4:
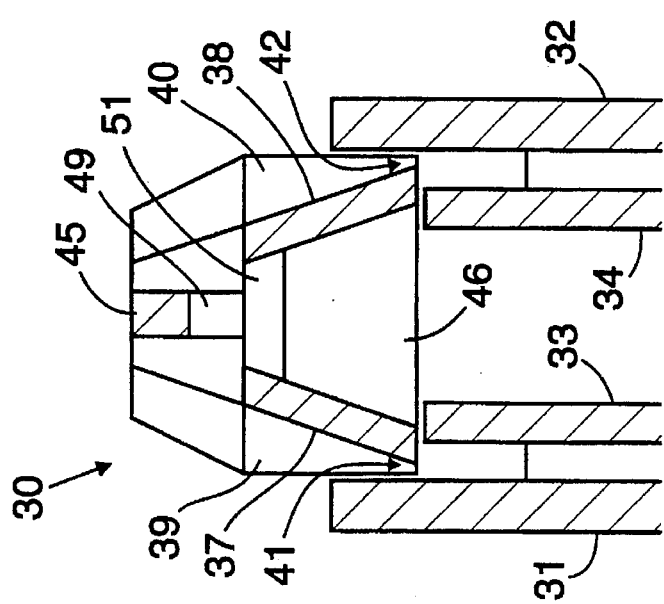
FIG. 4 is a cross section of the needle guide of FIG. 3 taken along the line 3—3 thereof.

FIGS. 3, 4 and 5 depict a needle guide 30 designed for use with two vertical slab gels in gel enclosures similar to that of FIG. 2. As shown in FIG. 4, the two enclosures are arranged to face each other with the taller plates 31, 32 on the outside and the shorter plates 33, 34 on the inside. Viewing FIGS. 3, 4 and 5 together, the needle guide 30 contains two sloping surfaces 37, 38, each interrupted by a series of transverse partitions 39, 40. The sloping surfaces both face outward, and the two series of partitions each extend outward in opposing directions away from the center of the guide. Each passage is thus defined by one of the sloping surfaces, two adjacent partitions, and the taller plate of the gel enclosure, the passage directing the syringe needle into one of the wells of the underlying gel. The guide thus differs from that of FIGS. 1 and 2 by lacking an opposing sloping surface to complete the fourth side of the passage, which is instead supplied by the taller plate of the gel enclosure. The passage still tapers however by virtue of its one sloping surface.

The partitions 39, 40 extend far enough from both sides of the guide to permit the guide to fit between the two taller plates 31, 32 while resting on the top edges of the two shorter plates 33, 34. The fit is loose enough to permit easy insertion and removal of the needle guide yet close enough to maintain the bottom openings 41, 42 of the guide in proper alignment with the gaps between the plates of the gel enclosures.

Further features of the needle guide depicted in FIGS. 3, 4 and 5 are a handle 45 extending longitudinally along the needle guide, and internal ribs at the center 46 and both ends 47, 48 of the guide. The ribs provide structural support to the guide as well as additional contact surfaces for resting the guide on the shorter gel enclosure plates. Beneath the handle are through passages 49, 50, 51, 52 making it easier for the user to grasp the handle.

The needle guides depicted in these figures can be used with any conventional vertical electrophoresis gel enclosure. An example is the PROTEAN II xi Cell, including the Multi-Cell and 2-D Cell models, and the Mini-PROTEAN II Electrophoresis System, all available from Bio-Rad Laboratories, Inc., Hercules, Calif., USA. The guides are likewise useful on gel enclosures from any of various other commercial suppliers. In each case, the dimensions of the guide are adapted for the particular gel enclosure on which the guide is to be used. As mentioned above, electrophoresis cells designed for gel enclosures with plates of unequal height generally use the taller plates as retaining walls for the upper buffer solution. In the arrangement shown in FIG. 4, the upper buffer solution is retained in a shallow receptacle of which the two tall plates 31, 32 for two opposing walls. A coolant chamber is often clamped between the gel enclosures, and the upper surface of the coolant chamber serves as the floor of the upper buffer receptacle.

In typical practice, the gel is polymerized between the two plates with a well-forming insert, referred to in the industry as a "comb" or a "template," resting along the open upper edges of the plates, the teeth of the comb extending into the space between the plates so that the gel forms beneath and between the teeth. Once the gel sets, the comb is removed to leave a row of wells along the top edge of the gel. Once the comb is removed, the needle guide of the present invention is inserted and samples are loaded into the wells with hypodermic syringes or other suitable injection devices. The needle guide is then removed, and the gel enclosure is joined to the other components of the electrophoresis cell to provide the electrical circuitry necessary to perform the electrophoresis. All of these procedures with the exception of the use of the needle guide are well known among those skilled in electrophoresis. Typical electrophoresis systems available commercially are supplied with a selection of combs varying in the number and width of the teeth. Needle guides can likewise be manufactured with a variety of partition spacings to correspond to the varying widths of the comb teeth.

The foregoing descriptions are offered primarily for purposes of illustration. It will be readily apparent to those skilled in the art that the structures of these needle guides and their manner of use can be further modified or substituted in various ways without departing from the spirit and scope of the invention. For example, the needle guide can be shaped for use with gel enclosures consisting of plates of equal height. Such a guide can be shaped to rest on top of and down the outer sides of both plates, rather than hooking over only one of the plates as shown in FIG. 2 or resting on the upper edges of two short plates and between two taller plates as shown in FIG. 4. Other variations are readily apparent.

We claim:

1. A needle guide for placing samples in wells along an upper edge of a slab-shaped electrophoresis gel retained in a gel enclosure defined by parallel vertical plates, said needle guide comprising:

a sloping surface;

a plurality of partitions extending transverse to said sloping surface to define passages corresponding to said wells;

means for stably resting said sloping surface and said partitions on said gel enclosure with said sloping surface sloping downward toward one of said parallel plates and said passages communicating with said wells.

2. A needle guide in accordance with claim 1 in which said parallel vertical plates are of unequal height thereby defining a tall plate and a short plate, and said means for stably resting said sloping surface and said partitions comprise means for holding said sloping surface in a position sloping downward toward said tall plate.

3. A needle guide in accordance with claim 2 in which said means for stably resting said sloping surface and said partitions comprise means for resting said sloping surface and said partitions over the upper edge of said tall plate.

4. A needle guide in accordance with claim 3 in which said means for resting said sloping surface and said partitions over the upper edge of said tall plate comprises an elongated inverted shoulder to rest on said upper edge of said tall plate.

5. A needle guide in accordance with claim 1 in which said gel enclosure comprises two pairs of vertical plates, each pair being parallel and of unequal height thereby defining a tall plate and a short plate, the two short plates facing each other, said needle guide comprising:

two said sloping surfaces on opposing sides of said guide and both outward facing; and two rows of partitions, one row thereof extending outward from each of said sloping surfaces.

6. A needle guide in accordance with claim 5 in which said means for stably resting said sloping surface and said partitions comprise means for resting said sloping surface and said partitions on the upper edges of the two short plates.

* * * * *